United States Patent [19]
Walt et al.

[11] Patent Number: 6,023,540
[45] Date of Patent: Feb. 8, 2000

[54] FIBER OPTIC SENSOR WITH ENCODED MICROSPHERES

[75] Inventors: David R. Walt, Lexington; Karri Lynn Michael, Somerville, both of Mass.

[73] Assignee: Trustees of Tufts College, Boston, Mass.

[21] Appl. No.: 08/818,199

[22] Filed: Mar. 14, 1997

[51] Int. Cl.$^7$ .................................................. G02B 6/26
[52] U.S. Cl. ..................... 385/12; 435/808; 430/800; 385/38; 385/147; 359/900
[58] Field of Search ................................. 385/12, 13, 31, 385/33, 38, 147, 901, 35; 359/368; 356/236; 435/808; 436/164, 172, 800, 805; 250/556

[56] References Cited

U.S. PATENT DOCUMENTS

| | | |
|---|---|---|
| 4,499,052 | 2/1985 | Fulwyer . |
| 4,822,746 | 4/1989 | Walt . |
| 5,002,867 | 3/1991 | Macevicz . |
| 5,028,545 | 7/1991 | Soini . |
| 5,105,305 | 4/1992 | Betzig et al. ............................. 359/368 |
| 5,114,864 | 5/1992 | Walt . |
| 5,132,242 | 7/1992 | Cheung ................................... 436/501 |
| 5,143,853 | 9/1992 | Walt et al. . |
| 5,194,300 | 3/1993 | Cheung ............................. 427/213.31 |
| 5,244,636 | 9/1993 | Walt et al. . |
| 5,244,813 | 9/1993 | Walt et al. . |
| 5,250,264 | 10/1993 | Walt et al. . |
| 5,252,494 | 10/1993 | Walt . |
| 5,254,477 | 10/1993 | Walt . |
| 5,298,741 | 3/1994 | Walt et al. . |
| 5,320,814 | 6/1994 | Walt et al. . |
| 5,496,997 | 3/1996 | Pope . |
| 5,512,490 | 4/1996 | Walt et al. . |
| 5,565,324 | 10/1996 | Still et al. ................................... 435/6 |
| 5,573,909 | 11/1996 | Singer et al. . |
| 5,633,972 | 5/1997 | Walt et al. . |
| 5,690,894 | 11/1997 | Pinkel et al. . |

FOREIGN PATENT DOCUMENTS

| | | |
|---|---|---|
| 0269764 | 6/1988 | European Pat. Off. . |
| 0478319 | 4/1992 | European Pat. Off. . |
| 0723146 | 7/1996 | European Pat. Off. . |
| WO8911101 | 11/1989 | WIPO . |
| WO9302360 | 2/1993 | WIPO . |
| WO9714028 | 4/1997 | WIPO . |

OTHER PUBLICATIONS

E.J.A.Pope, "Fiber Optic Chemical Microsensors Employing Optically Active Silica Microspheres", SPIE, v2388, p245–256 (1995).

J.I.Peterson, et al., "Fiber Optic pH Probe for Physiological Use", Anal. Chem., v52, No. 6, May 1980, p864–869.

Anonymous, "Fluorescent Microspheres", Tech Note 19, Bang Laboratories, (Fishers, IN) Feb. 1997.

L.B.Bangs, "Immunological Applications of Microspheres", The Latex Course, Bangs Laboratories (Carmel, IN) Apr. 1996.

Anonymous, "Microsphere Selection Guide", Bangs Laboratories (Fishers, IN) Sep. 1998.

*Primary Examiner*—Hung N. Ngo
*Attorney, Agent, or Firm*—Robin M. Silva; Flehr Hobach Test Albritton and Herbert LLP

[57] ABSTRACT

A microsphere-based analytic chemistry system is disclosed in which microspheres carrying different chemical functionalities may be mixed together while the ability is retained to identify the functionality on each bead using an optically interrogatable encoding scheme. An optical fiber bundle sensor is also disclosed in which the separate microspheres may be optically coupled to discrete fibers or groups of fibers within the bundle. The functionalies are encoded on the separate microspheres using fluorescent dyes and then affixed to wells etched in the end of the bundle. Thus, a single sensor may carry thousands of chemistries. Only those microspheres exhibiting reactions then need to be decoded to identify the corresponding functionality.

58 Claims, 7 Drawing Sheets

FIG._7A  BEFORE TAPPING

FIG._7B  AFTER TAPPING

FIG._8A  SIGNAL ONLY FROM ALKALINE PHOSPHATASE MICROSPHERES ex490/em530nm

FIG._8B  MIXTURE OF ENCODED MICROSPHERES ex577/em670nm

FIG._8C  MIXTURE OF ENCODED MICROSPHERES ex577/em610nm

SIGNAL ex490/em530nm

FIG._9A

ENCODED MICROSPHERES
ex577/em670nm

FIG._9B

Pre-Ag

FIG._10A

Post-Ag

FIG._10B

FIBER OPTIC SENSOR WITH ENCODED MICROSPHERES

BACKGROUND OF THE INVENTION

The use of optical fibers and optical fiber strands in combination with light absorbing dyes for chemical analytical determinations has undergone rapid development, particularly within the last decade. The use of optical fibers for such purposes and techniques is described by Milanovich et al., "Novel Optical Fiber Techniques For Medical Application", Proceedings of the SPIE 28th Annual International Technical Symposium On Optics and Electro-Optics, Volume 494, 1980; Seitz, W. R., "Chemical Sensors Based On Immobilized Indicators and Fiber Optics" in *C.R.C. Critical Reviews In Analytical Chemistry*, Vol. 19, 1988, pp. 135–173; Wolfbeis, O.S., "*Fiber Optical Fluorosensors In Analytical Chemistry*" in *Molecular Luminescence Spectroscopy, Methods and Applications* (S. G. Schulman, editor), Wiley & Sons, New York (1988); Angel, S. M., *Spectroscopy* 2(4):38 (1987); Walt, et al., "*Chemical Sensors and Microinstrumentation*", ACS Symposium Series, Vol. 403, 1989, p. 252, and Wolfbeis, O. S., *Fiber Optic Chemical Sensors*, Ed. CRC Press, Boca Raton, Fla., 1991, 2nd Volume.

When using an optical fiber in an in vitro/in vivo sensor, one or more light absorbing dyes are located near its distal end. Typically, light from an appropriate source is used to illuminate the dyes through the fiber's proximal end. The light propagates along the length of the optical fiber; and a portion of this propagated light exits the distal end and is absorbed by the dyes. The light absorbing dye may or may not be immobilized; may or may not be directly attached to the optical fiber itself; may or may not be suspended in a fluid sample containing one or more analytes of interest; and may or may not be retainable for subsequent use in a second optical determination.

Once the light has been absorbed by the dye, some light of varying wavelength and intensity returns, conveyed through either the same fiber or collection fiber(s) to a detection system where it is observed and measured. The interactions between the light conveyed by the optical fiber and the properties of the light absorbing dye provide an optical basis for both qualitative and quantitative determinations.

Of the many different classes of light absorbing dyes which conventionally are employed with bundles of fiber strands and optical fibers for different analytical purposes are those more common compositions that emit light after absorption termed "fluorophores" and those which absorb light and internally convert the absorbed light to heat, rather than emit it as light, termed "chromophores."

Fluorescence is a physical phenomenon based upon the ability of some molecules to absorb light (photons) at specified wavelengths and then emit light of a longer wavelength and at a lower energy. Substances able to fluoresce share a number of common characteristics: the ability to absorb light energy at one wavelength $\lambda_{ab}$; reach an excited energy state; and subsequently emit light at another light wavelength, $\lambda_{em}$. The absorption and fluorescence emission spectra are individual for each fluorophore and are often graphically represented as two separate curves that are slightly overlapping. The same fluorescence emission spectrum is generally observed irrespective of the wavelength of the exciting light and, accordingly, the wavelength and energy of the exciting light may be varied within limits; but the light emitted by the fluorophore will always provide the same emission spectrum. Finally, the strength of the fluorescence signal may be measured as the quantum yield of light emitted. The fluorescence quantum yield is the ratio of the number of photons emitted in comparison to the number of photons initially absorbed by the fluorophore. For more detailed information regarding each of these characteristics, the following references are recommended: Lakowicz, J. R., *Principles of Fluorescence Spectroscopy*, Plenum Press, New York, 1983; Freifelder, D., Physical Biochemistry, second edition, W. H. Freeman and Company, New York, 1982; "*Molecular Luminescence Spectroscopy Methods and Applications:* Part I" (S. G. Schulman, editor) in *Chemical Analysis*, vol. 77, Wiley & Sons, Inc., 1985; *The Theory of Luminescence*, Stepanov and Gribkovskii, Iliffe Books, Ltd., London, 1968.

In comparison, substances which absorb light and do not fluoresce usually convert the light into heat or kinetic energy. The ability to internally convert the absorbed light identifies the dye as a "chromophore." Dyes which absorb light energy as chromophores do so at individual wavelengths of energy and are characterized by a distinctive molar absorption coefficient at that wavelength. Chemical analysis employing fiber optic strands and absorption spectroscopy using visible and ultraviolet light wavelengths in combination with the absorption coefficient allow for the determination of concentration for specific analytes of interest by spectral measurement. The most common use of absorbance measurement via optical fibers is to determine concentration which is calculated in accordance with Beers' law; accordingly, at a single absorbance wavelength, the greater the quantity of the composition which absorbs light energy at a given wavelength, the greater the optical density for the sample. In this way, the total quantity of light absorbed directly correlates with the quantity of the composition in the sample.

Many of the recent improvements employing optical fiber sensors in both qualitative and quantitative analytical determinations concern the desirability of depositing and/or immobilizing various light absorbing dyes at the distal end of the optical fiber. In this manner, a variety of different optical fiber chemical sensors and methods have been reported for specific analytical determinations and applications such as pH measurement, oxygen detection, and carbon dioxide analyses. These developments are exemplified by the following publications: Freeman, et al., *Anal Chem.* 53: 98 (1983); Lippitsch et al., *Anal. Chem. Acta.* 205: 1, (1988); Wolfbeis et al., *Anal. Chem.* 60: 2028 (1988); Jordan, et al., *Anal. Chem.* 59: 437 (1987); Lubbers et al., *Sens. Actuators* 1983; Munkholm et al., *Talanta* 35: 109 (1988); Munkholm et al., *Anal. Chem.* 58: 1427 (1986); Seitz, W. R., *Anal. Chem.* 56: 16A-34A (1984); Peterson, et al., *Anal. Chem.* 52: 864 (1980): Saari, et al., *Anal. Chem.* 54: 821 (1982); Saari, et al., *Anal. Chem.* 55: 667 (1983); Zhujun et al., *Anal. Chem. Acta.* 160: 47 (1984); Schwab, et al., *Anal. Chem.* 56: 2199 (1984); Wolfbeis, O.S., "*Fiber Optic Chemical Sensors*", Ed. CRC Press, Boca Raton, Fla., 1991, 2nd Volume; and Pantano, P., Walt, D. R., *Anal. Chem.,* 481A-487A, Vol. 67, (1995).

More recently, fiber optic sensors have been constructed that permit the use of multiple dyes with a single, discrete fiber optic bundle. U.S. Pat. Nos. 5,244,636 and 5,250,264 to Walt, et al. disclose systems for affixing multiple, different dyes on the distal end of the bundle, the teachings of each of these patents being incorporated herein by this reference. The disclosed configurations enable separate optical fibers of the bundle to optically access individual dyes. This avoids the problem of deconvolving the separate signals in the returning light from each dye, which arises when the signals from two or more dyes are combined, each dye being sensitive to a different analyte, and there is significant overlap in the dyes' emission spectra.

SUMMARY OF THE INVENTION

The innovation of the two previous patents was the placement of multiple chemical functionalities at the end of a single optical fiber bundle sensor. This configuration yielded an analytic chemistry sensor that could be remotely monitored via the typically small bundle. The drawback, however, was the difficulty in applying the various chemistries associated with the chemical functionalities at the sensor's end; the functionalities were built on the sensor's end in a serial fashion. This was a slow process, and in practice, only tens of functionalities could be applied.

The present design is based on two synergistic inventions: 1) the development of a bead-based analytic chemistry system in which beads, also termed microspheres, carrying different chemical functionalities may be mixed together while the ability is retained to identify the functionality of each bead using an optically interrogatable encoding scheme; and 2) an optical fiber bundle sensor in which the separate beads or microspheres may be optically coupled to discrete fibers or groups of fibers within the bundle. Each invention has separate applications but, when implemented together, yields an optical fiber sensor that can support large numbers, thousands or more, of separate chemical functionalities, which is relatively easy to manufacture and use.

In general, according to one aspect, the invention concerns an analytic chemistry system that comprises a population of beads or microspheres. Within the population are separate subpopulations, each of which carries chemical functionality which changes an optical signature of the beads in a presence of targeted analytes. This signature change can occur via many different mechanisms. A few examples include the binding of a dye-tagged analyte to the bead, the production of a dye species on or near the beads, the destruction of an existing dye species, a change in optical signal upon analyte interaction with dye on bead, or any other optical interrogatable event. Although the subpopulations may be randomly mixed together, the chemical functionality on each bead is determined via an optical signature which is encoded with a description of the chemical functionality. As a result, by observing whether the optical signature of a particular bead is exhibiting a change, or not, and then decoding the signature for the functionality of the bead, the presence or not of the analyte targeted by the functionality may be determined.

In specific embodiments, the beads are encoded using dyes that are preferably entrapped within the beads, the chemical functionality being added on surfaces. The dyes may be chromophores or phosphors but are preferably fluorescent dyes, which due to their strong signals provide a good signal-to-noise ratio for decoding. The encoding can be accomplished in a ratio of at least two dyes, although more encoding dimensions may be added in the size of the beads, for example.

According to another aspect, the invention also concerns an analytic chemistry fiber optic bundle sensor. This sensor has a population of beads carrying chemical functionalities at, on or near, a distal end of the bundle. The ability to monitor optical signature changes associated with individual or multiple beads is provided by coupling those signature changes into separate optical fibers or groups of fibers of the bundle for transmission to the proximal end where analysis is performed either manually, by the user, or automatically, using image processing techniques.

In the preferred embodiment, each one of the beads is located within separate wells formed at terminal ends of optical fibers of the bundle. These microwells are formed by anisotropic etching of the cores of the optical fibers with respect to the cladding.

Also in the preferred embodiment, the population of beads includes separate subpopulations, typically randomly distributed in an array across the bundle end, each subpopulation carrying a different chemical functionality and an optically interrogatable code descriptive of the chemical functionality.

Although each sensor is different insofar that it has a different distribution of the subpopulations of beads within its wells, only those beads that exhibit a positive optical response or signature change need to be decoded. Therefore, the burden is placed on the analysis rather than on sensor manufacture. Moreover, since the beads and fibers in the array can be monodisperse, the fluorescent regions arising from signal generation are extremely uniform and can be analyzed automatically using commercially available microscopy analysis software, such image processing software is capable of defining different spectral regions automatically and counting the number of segments within each region in several seconds.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

1. Microspheres

Figure 1:
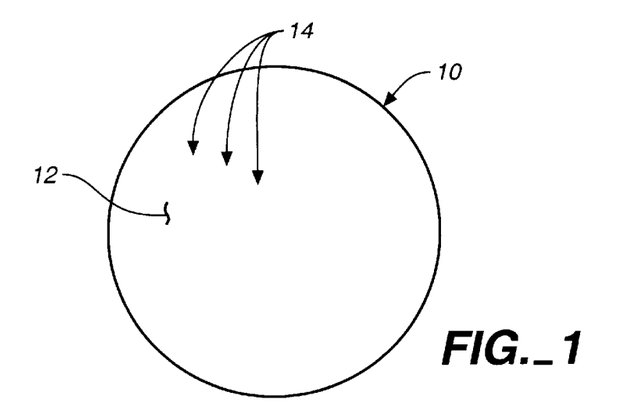
FIG. 1 is a schematic diagram illustrating the optical signature encoding and chemical functionalizing of the microspheres according to the present invention.

FIG. 1 illustrates the construction of a bead or microsphere 10 according to the principles of the present invention. In common with the prior art, the microsphere 10 is given a chemical functionality 12, which is typically applied to the microsphere's surface. The chemical functionality is designed so that in the presence of the analyte(s) to which it is targeted, an optical signature of the microsphere, possibly including region surrounding it, is changed.

The bead or microsphere need not be spherical, irregular beads may be used. They are typically constructed from plastic or ceramic, and bead sizes ranging from nanometers, e.g., 500 nm, to millimeters, e.g., 1 mm, may be used. Moreover, various bead chemistries may be used. Beads or microspheres comprising methylstyrene, polystyrene, acrylic polymer, latex, paramagnetic, thoria sol, carbon graphite, and titanium dioxide are various possibilities. "*Microsphere Detection Guide*" from Bangs Laboratories, Fishers Ind. is a helpful guide.

The inventive microsphere has an optical signature that is encoded with a description of the chemical functionality. In the preferred embodiment, reporter dyes 14 are added to the microsphere 10 with the encoding occurring in the ratio of two or more dyes. The reporter dyes 14 may be chromophore-type. Fluorescent dyes, however, are preferred because the strength of the fluorescent signal provides a better signal-to-noise ratio when decoding. Additionally, encoding in the ratios of the two or more dyes, rather than single dye concentrations, is preferred since it provides insensitivity to the intensity of light used to interrogate the reporter dye's signature and detector sensitivity.

Figure 2:
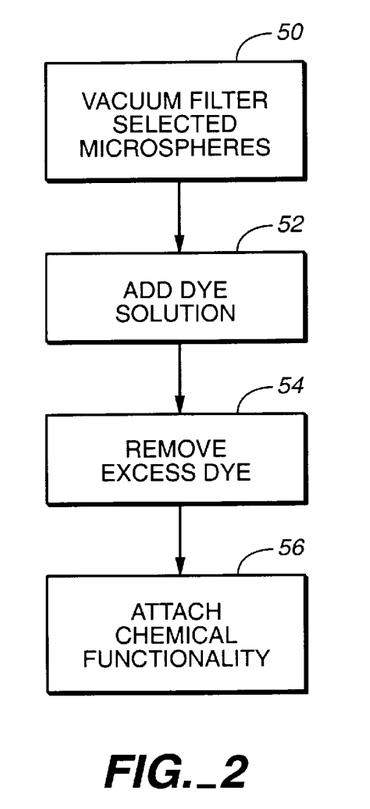
FIG. 2 is a process diagram describing the preparation, encoding, and functionalizing of the microspheres of the present invention.

FIG. 2 is a process diagram illustrating the preparation of the microspheres. In step 50, an aliquot of stock microspheres are vacuum filtered to produce a dry cake. In one implementation, microspheres of methylstyrene (87%) and divinylbenzene (13%) are used that have a 3.1 micrometer ($\mu$m) diameter.

The microspheres may be purchased with the desired chemical functionalities already present. A large selection of such pre-prepared microspheres are currently available from a number of commercial vendors. Alternatively, "blank" microspheres may be used that have surface chemistries that facilitate the attachment of the desired functionality by the user. Some examples of these surface chemistries for blank microspheres are listed in Table I.

TABLE I

| Surface chemistry | Name: |
|---|---|
| $NH_2$ | Amine |
| COOH | Carboxylic Acid |
| CHO | Aldehyde |
| $CH_2$—$NH_2$ | aliphatic Amine |
| CO $NH_2$ | Amide |
| $CH_2$—Cl | Chloromethyl |
| CONH-$NH_2$ | Hydrazide |
| OH | Hydroxyl |
| $SO_4$ | Sulfate |
| $SO_3$ | Sulfonate |
| Ar $NH_2$ | Aromatic Amine |

The dry cake is then broken apart and a dye solution added to it in step 52 to encode optical signatures of the microspheres with information concerning the intended surface chemical functionalities. Dyes may be covalently bonded to the microspheres' surface, but this consumes surface binding sites desirably reserved for the chemical functionalities. Preferably, the microspheres are placed in a dye solution comprising a ratio of two or more fluorescent reporter dyes dissolved in an organic solvent that will swell the microspheres, e.g., dimethylformamide (DMF). The length of time the microspheres are soaked in the dye solution will determine their intensity and the broadness of the ratio range. Longer times yield higher intensities, but broader ratio ranges.

In an exemplary two dye system, Texas Red Cadaverine (TRC) is used, which is excited at $\lambda_{ab}$=580 mm and emits at $\lambda_{em}$=630 mm, in combination with indodicarbocyanine (DiIC): 610/670 ($\lambda_{ab}/\lambda_{em}$). Generally, dyes are selected to be compatible with the chemistries involved in the analysis and to be spectrally compatible. The emission wavelengths of the dyes should not overlap the regions of the optical spectrum in which the chemical functionalities induce changes in the microsphere signatures. This avoids deconvolution problems associated with determining signal contributions based on the presence of both the analyte and the encoding dye ratios contributing to an overlapping emission spectral region.

Examples of other dyes that can be used are Oxazin (662/705), IR-144 (745/825), IR-140 (776/882), IR-125 (786/800) from Exiton, and Bodipy 665/676 from Molecular Probes, and Naphthofluorescein (605/675) also from Molecular Probes. Lanthide may also be used. Fluorescent dyes emitting in other than the near infrared may also be used. Chromophore dyes are still another alternative that produce an optically interrogatable signature, as are more exotic formulations using Raman scattering-based dyes or polarizing dyes, for example.

The ability of a particular dye pair to encode for different chemical functionalities depends on the resolution of the ratiometric measurement. Conservatively, any dye pair should provide the ability to discriminate at least twenty different ratios. The number of unique combinations of two dyes made with a particular dye set is shown in the following Table II.

TABLE II

| Number of dyes in set | Combinations possible |
|---|---|
| 3 | 3 |
| 4 | 6 |

TABLE II-continued

| Number of dyes in set | Combinations possible |
| --- | --- |
| 5 | 10 |
| 6 | 15 |

Thus, using six dyes and twenty distinct ratios for each dye pair, 300 separate chemical functionalities may be encoded in a given population of microspheres. Combining more than two dyes provides additional diversity in the encoding combinations.

It should be understood that surface chemistries may be present throughout the microsphere's volume, and not limited to the physical circumferential surface.

In the prior art, a large spectrum of chemical functionalities have been manifest on microspheres that produce optically interrogatable changes in the presence of the targeted analyte. These functionalities include four broad classifications of microsphere sensors: 1) basic indicator chemistry sensors; 2) enzyme-based sensors; 3) immuno-based sensors; and 3) geno-sensors.

A large number of basic indicator microsphere sensors have been previously demonstrated. Examples include:

TABLE III

| TARGET ANALYTE | CHEMICAL FUNCTIONALITY | NOTES ($\lambda_{ab}/\lambda_{em}$) |
| --- | --- | --- |
| pH Sensors based on: | seminaphthofluoresceins | e.g., carboxy-SNAFL |
|  | seminaphthorhodafluors | e.g., carboxy-SNARF |
|  | 8-hydroxypyrene-1,3,6-trisulfonic acid |  |
|  | fluorascein |  |
| CO2 Sensors based On: | seminaphthofluoresceins | e.g., carboxy-SNAFL |
|  | seminaphthorhodafluors | e.g., carbody-SNARF |
|  | 8-hydroxypyrene-1,3,6-trisulfonic acid |  |
| Metal Ions Sensors based On: | desferriozamine B | e.g., Fe |
|  | cyclen derivatives | e.g., Cu, Zn |
|  | derivatizad peptides | e.g., FITC-Gly-Gly-His, and FITC-Gly His, Cu, Zn |
|  | fluorexon (calcine) | e.g., Ca, Mg, Cu, Pb, Ba |
|  | calcine blue | e.g., Ca, Mg, Cu |
|  | methyl calcine blue | e.g., Ca, Mg, Cu |
|  | ortho-dianisidine tetracetic acid (ODTA) | e.g., Zn |
|  | bis-salicylidene ethylenediamine (SED) | e.g., Al |
|  | N-(6-methoxy-8-quinolyl-p-toluenesulfonamine (TSQ) | e.g., Zn |
|  | Indo-1 | e.g., Mn, Ni |
|  | Fura-2 | e.g., Mn, Ni |
|  | Magnesium Green | e.g., Mg, Cd, Tb |
|  | Siphenyliaobenzofuran | 409/476 |
|  | Methoxyvinyl pyrene | 352/401 |
| Nitrite | diaminonaphthaline | 340/377 |
| NO | luminol | 355/411 |
|  | dihydrohodamine | 289/none |
| $Ca^{2+}$ | Pia-fura | 340/380 |
|  | Calcium Green | visible light/530 |
|  | Fura-2 | 340/380 |
|  | Indo-1 | 405/485 |
|  | Fluo-3 | visible light/525 |
|  | Rhod-2 | visible light/570 |
| $Mg^{2+}$ | Mag-Fura-2 | 340/380 |
|  | Mag-Fura-5 | 340/380 |
|  | Meg-Indo-1 | 405/485 |
|  | Magnesium Green | 475/530 |
|  | Magnesium Orange | visible light/545 |
| $Zn^{2+}$ | Newport Green | 506/535 |
| TSQ | Methoxy-Quinobyl | 334/385 |
| $Cu^+$ | Phen Green | 492/517 |
| $Na^+$ | SBFI | 339/565 |
|  | SBFO | 354/575 |
|  | Sodium Green | 506/535 |
| $K^+$ | PBFI | 336/587 |
| $Cl^-$ | SPQ | 344/443 |
|  | MQAE | 350/460 |

In step 54, the microspheres are vacuum filtered to remove excess dye. The microspheres are then washed in water or other liquid that does not swell the microspheres, but in which the dyes are still soluble. This allows the residual dye to be rinsed off without rinsing the dye out of the microspheres.

In step 56, the chemical functionality is attached to the microsphere surface chemistries if not already present.

Each of the chemicals listed in Table III directly produces an optically interrogatable signal or optical signature change in the presence of the targeted analyte.

Enzyme-based microsphere sensors have also been demonstrated and could be manifest on microspheres. Examples include:

TABLE IV

| SENSOR TARGET | CHEMICAL FUNCTIONALITY |
|---|---|
| Glucose Sensor | glucose oxidase (enz.) + $O_2$-sensitive dye (see TABLE I) |
| Penicillin Sensor | penicillinase (enz.) + pH-sensitive dye (see TABLE I) |
| Urea Sensor | urease (enz.) + pH-sensitive dye (see. TABLE I) |
| Acetylcholine Sensor | acetylcholinesterase (enz.) + pH-sensitive dye (see TABLE I) |

(e.g., mycoplasmal pneumonia), Protozoal (e.g., amoebiasis, toxoplasmosis), Rickettsial (e.g., Rock Mountain spotted fever), and pregnancy tests.

Microsphere genosensors have also been demonstrated. These are typically constructed by attaching a probe sequence to the microsphere surface chemistry, typically via an $NH_2$ group. A fluorescent dye molecule, e.g., fluorescein, is attached to the target sequence, which is in solution. The optically interrogatable signature change occurs with the binding of the target sequences to the microsphere. This produces a higher concentration of dye surrounding the microsphere than in the solution generally. A few demonstrated probe and target sequences, see Ferguson, J. A. et al. *Nature Biotechnology*, Vol. 14, Dec. 1996, are listed below in Table V.

TABLE V

| PROBE SEQUENCES | TARGET SEQUENCES |
|---|---|
| B-glo(+) (segment of human B-globin)5'-$NH_2$—$(CH_2)_8$—)TT TTT TTT TCA ACT TCA TCC ACG TTC ACC-3 | B-glo(+)-CF 5'-Fluorescein-TC AAC GTG GAT GAA GTT C-3' |
| IFNG(interferon gamma 1)5'-$NH_2$— $(CH_2)_8$—$T_{12}$—TGG CTT CTC TTG GCT GTT ACT-3' | IFNG-CF 5'-Fluorescein-AG TAA CAG CCA AGA GAA CCC AAA-3' |
| 1L2 (interleukin-2)5'-$NH_2$—$(CH_2)_8$— $T_{12}$—TA ACC GAA TCC CAA ACT CAC CAG-3' | 1L2-CF 5'-Fluorescein-CT GGT GAG TTT GGG ATT CTT GTA-3' |
| 1L4 (interleukin-4)5'$NH_2$—$(CH_2)_8$— $T_{12}$—CC AACTGC TTC CCC CTC TGT-3' | 1L4-CF 5'-Fluorescein-AC AGA GGG GGA AGC AGT TGG-3' |
| 1L6 (interleukin-6)5'$NH_2$—$(CH_2)_8$—$T_{12}$— GT TGG GTC AGG GGT GGT TAT T-3' | 1L6-CF 5'-Fluorescein - AA TAA CCA CCC CTG ACC CAA C-3' |

Generally, the induced change in the optical signature due to the presence of the enzyme-sensitive chemical analyte occurs indirectly in this class of chemical functionalities. The microsphere-bound enzyme, e.g., glucose oxidase, decomposes the target analyte, e.g., glucose, consume a co-substrate, e.g., oxygen, or produce some by-product, e.g., hydrogen peroxide. An oxygen sensitive dye is then used to trigger the signature change.

Techniques for immobilizing enzymes on microspheres, are known in the prior art. In one case, $NH_2$ surface chemistry microspheres are used. Surface activation is achieved with a 2.5% glutaraldehyde in phosphate buffered saline (10 mM) providing a pH of 6.9. (138 mM NaCl, 2.7 mM, KCl). This is stirred on a stir bed for approximately 2 hours at room temperature. The microspheres are then rinsed with ultrapure water plus 0.01% tween 20 (surfactant) −0.02%, and rinsed again with a pH 7.7 PBS plus 0.01% tween 20. Finally, the enzyme is added to the solution, preferably after being prefiltered using a 0.45 μm amicon micropure filter.

Immuno-based microsphere sensors have been demonstrated for the detection for environmental pollutants such as pesticides, herbicides, PCB's and PAH's. Additionally, these sensors have also been used for diagnostics, such as bacterial (e.g., leprosy, cholera, lyme disease, and turburculosis), viral (e.g., HIV, herpes simplex, cytomegalovirus), fungal (e.g., aspergillosis, candidiasis, cryptococcoses), Mycoplasmal Alternatively, upon binding of the target sequences, an intercalating dye (e.g., ethidium bromide) can be added subsequently to signal the presence of the bound target to the probe sequence.

Figure 3:
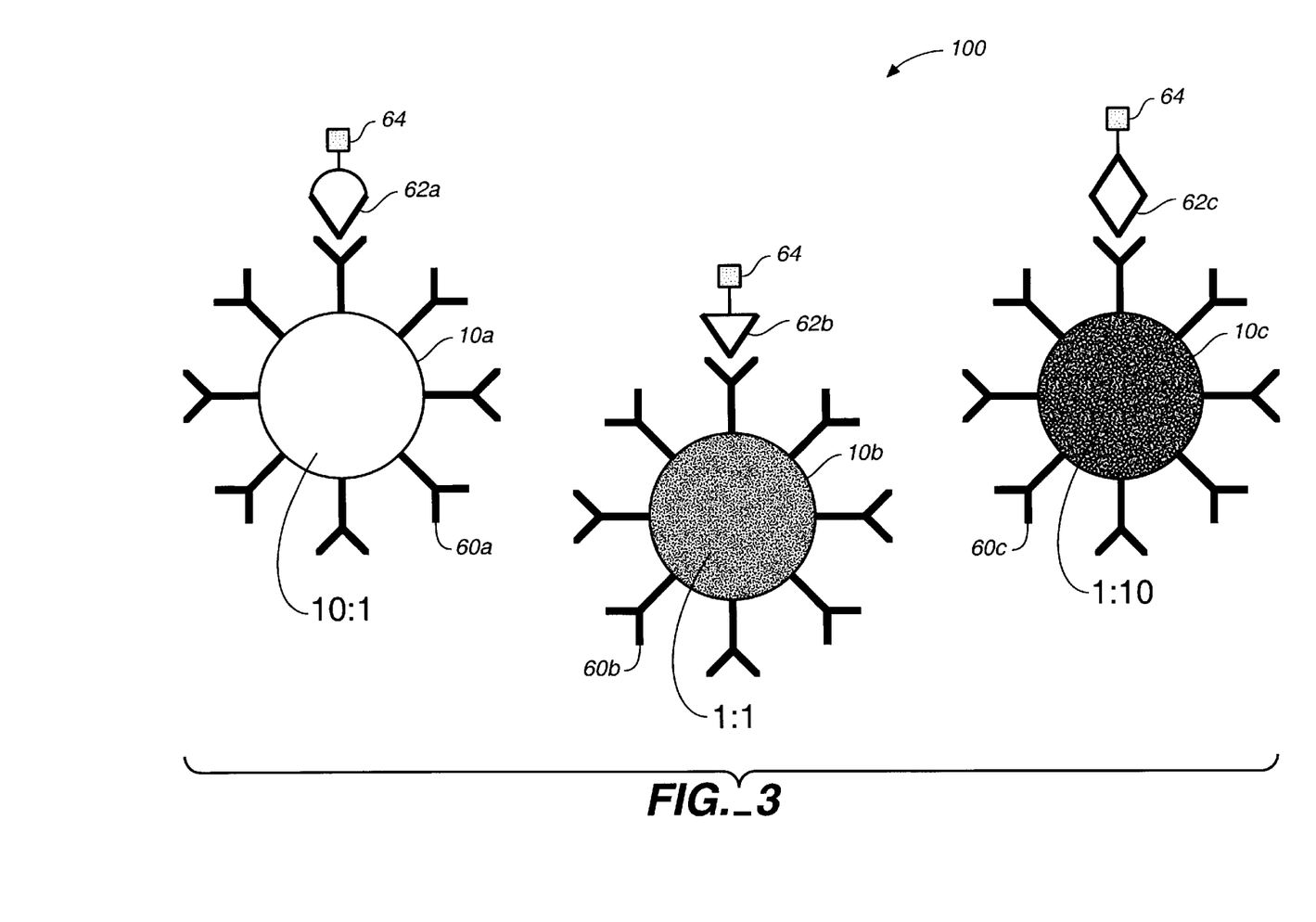
FIG. 3 is a schematic diagram illustrating a microsphere system including microspheres with different chemical functionalities and encoded descriptions of the functionalities.

FIG. 3 illustrates the construction of an analytic chemistry system 100 from microspheres that have different chemical functionalities. Subpopulations of microspheres are represented as 10a, 10b, 10c carrying respective probe sequences 60a, 60b, 60c, as exemplary functionalities. These subpopulations, once manufactured, are combined and mixed with each other. The resulting combined population contains microspheres with randomly distributed individual chemical functionalities.

Typically, mixing microspheres with different functionalities results in the loss of information regarding the selectivity for each of the corresponding target sequences. In a solution of microspheres with each of the probe sequences 60a, 60b, and 60c, it is possible to determine that at least one of the target sequences 62a, 62b, and 62c is present when a fluorescent marker dye 64 concentration is observed on the microspheres 10. There is no way, however, to determine which probe sequence 60a, 60b, and 60c is generating the activity since the information concerning which microsphere contained which probe sequence was lost when the subpopulations were mixed.

In contrast, in the present invention, each microsphere in each subpopulation is encoded with a common optical signature. In the illustrated example, the subpopulation represented by microsphere 10a has a two reporter dye ratio of 10:1; the subpopulation of microspheres 10b has a ratio of 1:1 of the same reporter dyes, and subpopulation of microspheres 10c has a ratio of 1:10 of the reporter dyes.

Thus, the randomly mixed subpopulations of microspheres are useful as an analytic chemistry system based on each of the carried chemical functionalities 60a–60c separately. The system 100 is added to an analyte of interest to which some of the chemical functionalities may interact. Any interaction changes the optical response of the corresponding microspheres by, for example, binding a fluorescent dye 64 to the microspheres. By identifying the chemical functionalities of the microsphere in which the optical signature has changed, using the encoded dye combinations, information regarding the chemical identity and concentration of the analyte may be gained based upon the interaction or noninteraction of each functionality contained in the probe 100.

The microspheres exhibiting activity or changes in their optical signature may be identified by utilizing a somewhat "manual" approach of observing the individual microspheres through a microscope. Decoding can also be performed manually, depending on the particular reporter dyes used. It may be helpful to use optical aids such as light filters to observe the light from the microspheres at emission wavelengths of the reporter dyes. While this approach is possible, in the preferred embodiment, the analytic chemistry microsphere system is used with the inventive optical fiber sensor.

2. Optical Fiber Sensor

Figure 4:
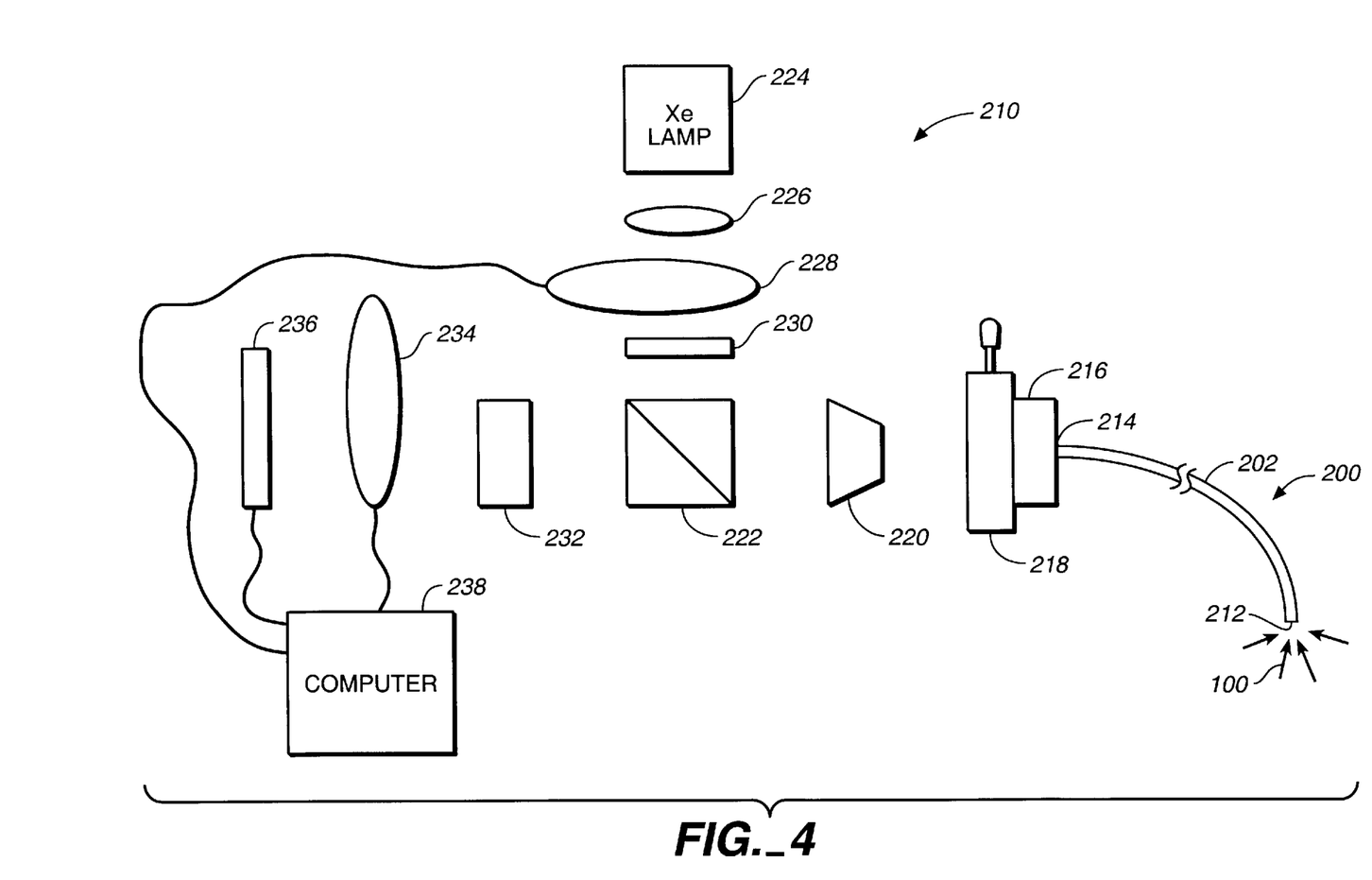
FIG. 4 is a schematic diagram of the inventive fiber optic sensor and associated instrumentation and control system.

FIG. 4 is a schematic block diagram showing the inventive optical fiber sensor 200 and associated control system 210. The fiber optic sensor 200 comprises a fiber optic bundle 202, that is constructed from separately clad fibers so that light does not mix between fibers. The microsphere system 100 is attached to the bundle's distal end 212, with the proximal end 214 being received by a z-translation stage 216 and x-y micropositioner 218. These two components act in concert to properly position the proximal end 214 of the bundle 202 for a microscope objective lens 220. Light collected by the objective lens 220 is passed to a reflected light fluorescence attachment with three pointer cube slider 222. The attachment 222 allows insertion of light from a 75 Watt Xe lamp 224 through the objective lens 220 to be coupled into the fiber bundle 202. The light from the source 224 is condensed by condensing lens 226, then filtered and/or shuttered by filter and shutter wheel 228, and subsequently passes through a ND filter slide 230.

Light returning from the distal end 212 of the bundle 202 is passed by the attachment 222 to a magnification changer 232 which enables adjustment of the image size of the fiber's proximal or distal end. Light passing through the magnification changer 232 is then shuttered and filtered by a second wheel 234. The light is then imaged on a charge coupled device (CCD) camera 236. A computer 238 executes imaging processing software to process the information from the CCD camera 236 and also possibly control the first and second shutter and filter wheels 228, 234. The instrumentation exclusive of the fiber sensor 200, i.e., to the left of the proximal end of the bundle 202 is discussed more completely by Bronk, et al., *Anal. Chem.* 1995, Vol. 67, number 17, pp. 2750–2752.

The microsphere system 100 may be attached to the distal end of the optical fiber bundle using a variety of compatible processes. It is important that the microspheres are located close to the end of the bundle. This ensures that the light returning in each optical fiber predominantly comes from only a single microsphere. This feature is necessary to enable the interrogation of the optical signature of individual microspheres to identify reactions involving the microsphere's functionality and also to decode the dye ratios contained in those microspheres. The adhesion or affixing technique, however, must not chemically insulate the microspheres from the analyte.

Figure 5A:
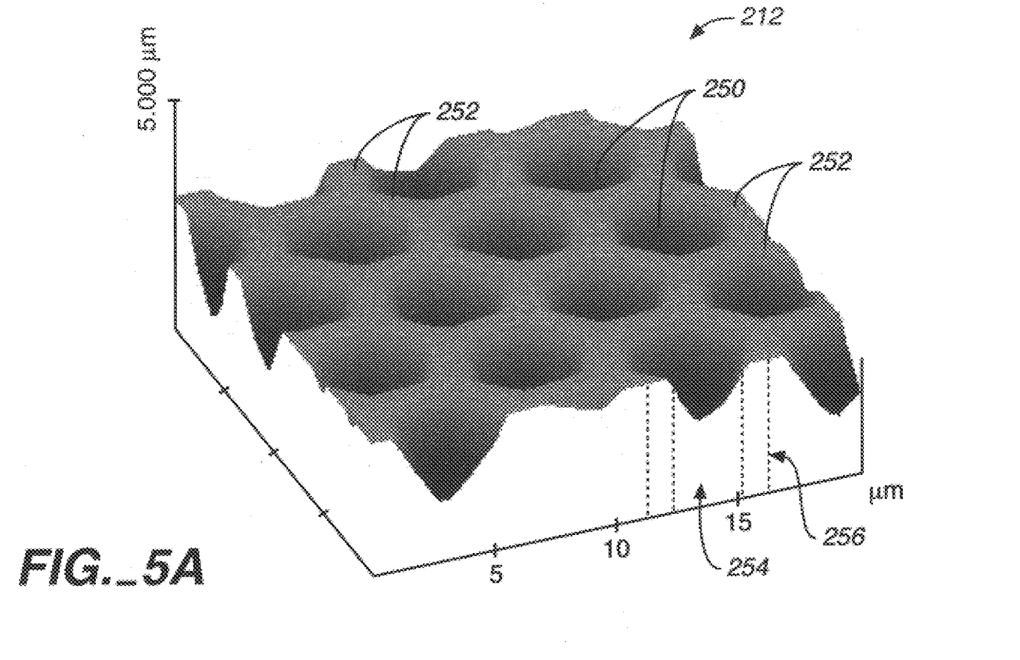
FIGS. 5A and 5B are micrographs illustrating the preferred technique for attaching or affixing the microspheres to the distal end of the optical fiber bundle.
Figure 5B:
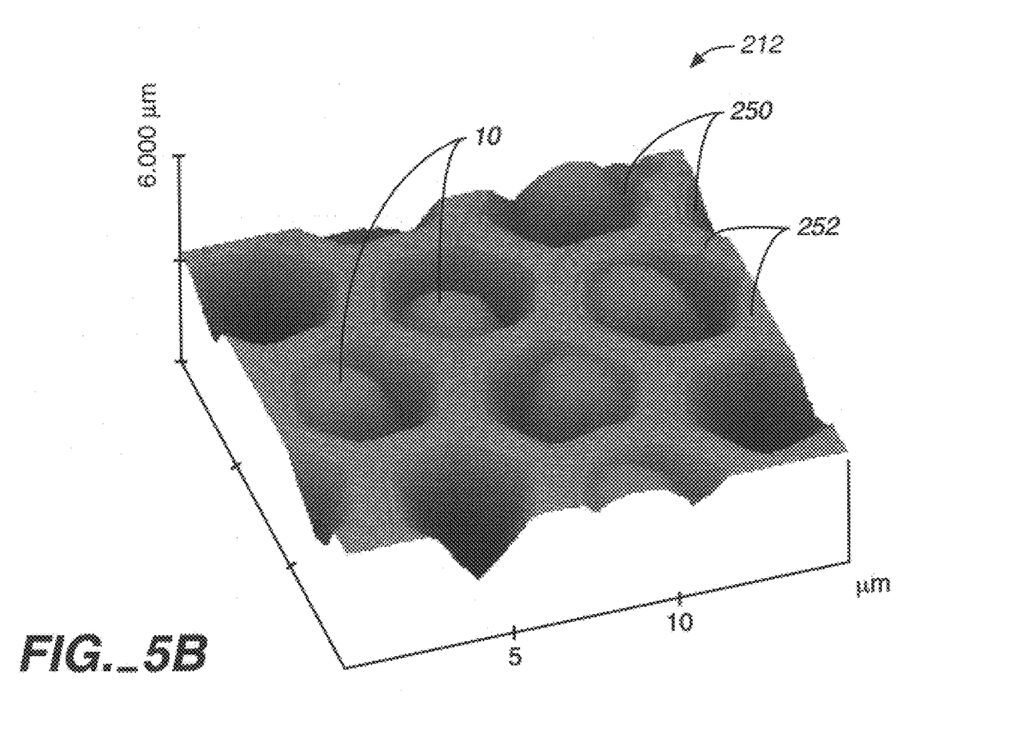

FIGS. 5A and 5B are micrographs of the distal end 212 of the bundle 202 illustrating the preferred technique for attaching the microspheres 10 to the bundle 202. Wells 250 are formed at the center of each optical fiber 252 of the bundle 202. As shown in FIG. 5B, the size of the wells 250 are coordinated with the size of the microspheres 10 so that the microspheres 10 can be placed within the wells 250. Thus, each optical fiber 252 of the bundle 202 conveys light from the single microsphere 10 contained in its well. Consequently, by imaging the end of the bundle 202 onto the CCD array 236, the optical signatures of the microspheres 10 are individually interrogatable.

Figure 6:
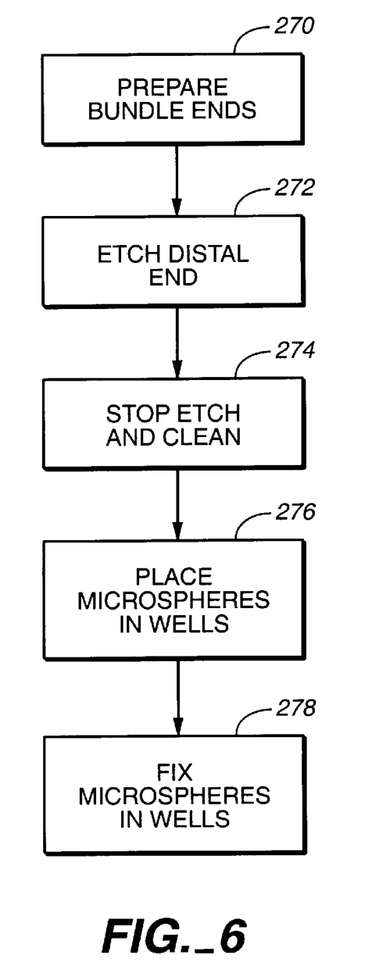
FIG. 6 is a process diagram describing well formation in the optical fiber bundle and affixation of the microspheres in the wells.

FIG. 6 illustrates how the microwells 250 are formed and microspheres 10 placed in the wells. A 1 mm hexagonally-packed imaging fiber contains approximately 20,600 individual optical fibers that have cores approximately 3.7 $\mu$m across (Part No. ET26 from Galileo Fibers). Typically, the cores of each fiber are hexagonally shaped as a result of glass hardness and drawing during fiber fabrication. In some cases, the shape can be circular, however.

In step 270, both the proximal and distal ends 212,214 of the fiber bundle 202 are successively polished on 12 $\mu$m, 9 $\mu$m, 3 $\mu$m, 1 $\mu$m, and 0.3 $\mu$m lapping films. Subsequently, the ends can be inspected for scratches on an atomic force microscope. In step 272, etching is performed on the distal end 212 of the bundle 202. A solution of 0.2 grams $NH_4F$ (ammonium fluoride) with 600 $\mu$l $dH_2O$ and 100 $\mu$l of HF (hydrofluoric acid), 50% stock solution, may be used. The distal end 212 is etched in this solution for a specified time, preferably approximately 80 seconds.

Upon removal from this solution, the bundle end is immediately placed in deionized water to stop any further etching in step 274. The fiber is then rinsed in running tap water. At this stage, sonication is preferably performed for several minutes to remove any salt products from the reaction. The fiber is then allowed to air dry.

The foregoing procedure produces wells by the anisotropic etching of the fiber cores 254 favorably with respect to the cladding 256 for each fiber of the bundle 202. The wells have approximately the diameter of the cores 254, 3.7 $\mu$m. This diameter is selected to be slightly larger than the diameters of the microspheres used, 3.1 $\mu$m, in the example. The preferential etching occurs because the pure silica of the cores 254 etches faster in the presence of hydrofluoric acid than the germanium-doped silica claddings 256.

The microspheres are then placed in the wells 250 in step 276 according to a number of different techniques. The placement of the microspheres may be accomplished by dripping a solution containing the desired randomly mixed subpopulations of the microspheres over the distal end 212, sonicating the bundle to settle the microspheres in the wells, and allowing the microsphere solvent to evaporate. Alternatively, the subpopulations could be added serially to the bundle end. Microspheres 10 may then be fixed into the wells 250 by using a dilute solution of sulfonated Nafion that is dripped over the end. Upon solvent evaporation, a thin film of Nafion was formed over the microspheres which holds them in place. This approach is compatible for fixing microspheres for pH indication that carry FITC functionality. The resulting array of fixed microspheres retains its pH sensitivity due to the permeability of the sulfonated Nafion to hydrogen ions. This approach, however, can not be employed generically as Nafion is impermeable to most water soluble species. A similar approach can be employed with different polymers. For example, solutions of polyethylene glycol, polyacrylamide, or polyhydroxymethyl methacrylate (polyHEMA) can be used in place of Nafion, providing the requisite permeability to aqueous species.

An alternative fixation approach employs microsphere swelling to entrap each microsphere 10 in its corresponding microwell 250. In this approach, the microspheres are first distributed into the microwells 250 by sonicating the microspheres suspended in a non-swelling solvent in the presence of the microwell array on the distal end 212. After placement into the microwells, the microspheres are subsequently exposed to an aqueous buffer in which they swell, thereby physically entrapping them, analogous to muffins rising in a muffin tin.

One of the most common microsphere formations is tentagel, a styrene-polyethylene glycol co-polymer. These microspheres are unswollen in nonpolar solvents such as hexane and swell approximately 20–40% in volume upon exposure to a more polar or aqueous media. This approach is extremely desirable since it does not significantly compromise the diffusional or permeability properties of the microspheres themselves.

Figure 7A:
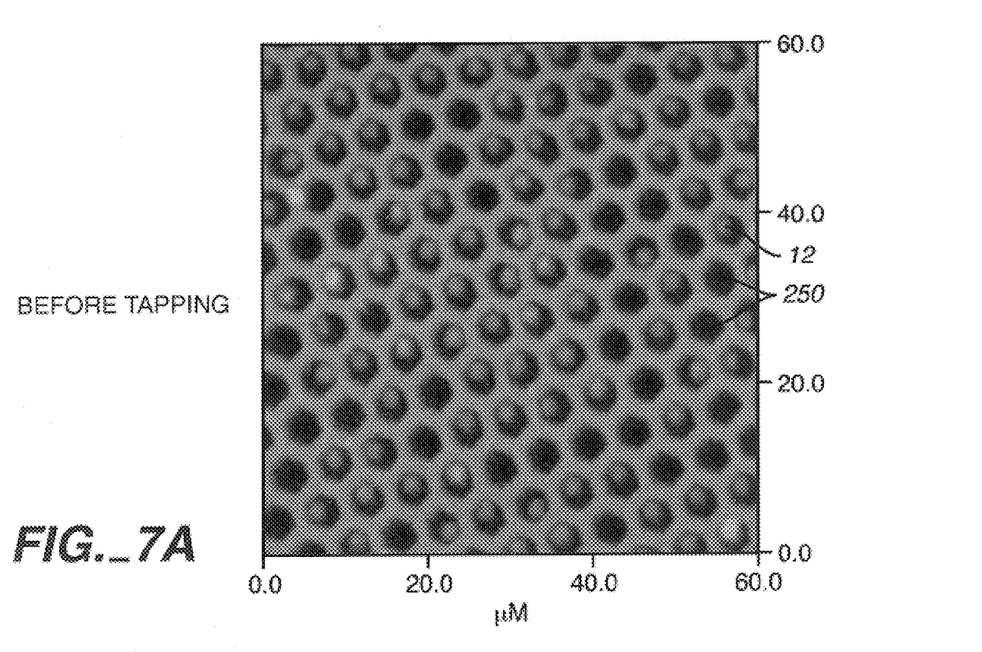
FIGS. 7A and 7B are micrographs showing the array of microspheres in their corresponding wells prior and subsequent to physical agitation, tapping and air pulsing, demonstrating the electrostatic binding of the microspheres in the wells.
Figure 7B:
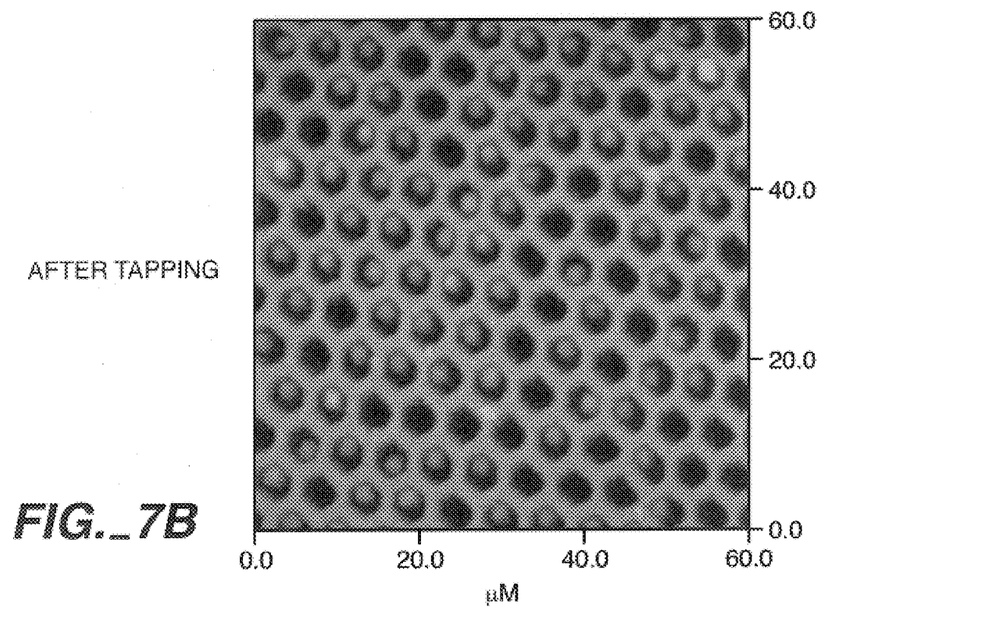

FIGS. 7A and 7B show polymer coated microspheres 12 in wells 250 after their initial placement and then after tapping and exposure to air pulses. FIGS. 7A and 7B illustrate that there is no appreciable loss of microspheres from the wells due to mechanical agitation even without a specific fixing technique. This effect is probably due to electrostatic forces between the microspheres and the optical fibers. These forces tend to bind the microspheres within the wells. Thus, in most environments, it may be unnecessary to use any chemical or mechanical fixation for the microspheres.

In alternative embodiments, additional encoding parameters can be added, such as microsphere size. If a number of sensors needed exceeds a few hundred, it is possible to use microspheres of different sizes to expand the encoding dimensions of the microspheres. Optical fiber arrays can be fabricated containing pixels with different fiber diameters. With different diameters, the largest wells can be filled with the largest microspheres and then moving onto progressively smaller microspheres in the smaller wells until all size wells are then filled. In this manner, the same dye ratio could be used to encode microspheres of different sizes thereby expanding the number of different oligonucleotide sequences or chemical functionalities present in the array.

Experimental Results
Enzyme-Based Sensor
  Subpopulation A
  Chemical functionality: Alkaline phosphatase
  Target substrate: fluorescein diphosphate (FDP)
  Reported dye ratio: 1:1 ratio of DiIC:TRC, where DiIC is 1,1',3,3,3',3'-hexamethyl-indodicarbocyanine iodide and TRC is Texas Red cadaverine
A range of ratios of light intensities are selected that are representative of the optical signature for the dye ratio of the subpopulation based on the quantum yield of the two dyes. The optical signature for this subpopulation is:

$$\frac{iIC\lambda \text{ intensity} - ave.\ DiIC \text{ background}}{TRC\lambda \text{ intensity} - ave.\ TRC \text{ background}} = 0.847 \pm 0.23$$

Subpopulation B
  Chemical functionality: B-Galactosidase;
  Target substrate=fluorescein di-B-galactopyranoside (FDG)
  Reporter dye ratio: 10:1 ratio of DiIC:TRC which translates to an optical signature of:

$$\frac{DiIC\lambda \text{ intensity} - ave.\ DiIC \text{ background}}{TRC\lambda \text{ intensity} - ave.\ TRC \text{ background}} = 4.456 \pm 1.27.$$

Subpopulation C
  Chemical functionality: B-glucuronidase
  Target substrate=fluorescein di-B-D-glucuronide (FDGicu).
  Reporter dye ratio: 1:10 ratio of DiIC:TRC, which translates to an optical signature of:

$$\frac{DiIC\lambda \text{ intensity} - ave.\ DiIC \text{ background}}{TRC\lambda \text{ intensity} - ave.\ TRC \text{ background}} = 0.2136 \pm 0.03.$$

When the microsphere populations are in the presence of one or more of the substrates, the respective enzymes on the microspheres catalyze the breakdown of the substrates producing fluorescein which is fluorescent, emitting light at 530 nanometers when excited at 490 nm. The production of fluorescein localized to particular beads is then monitored. In this approach, the localization of fluorescein around the microspheres is increased by using a substrate solution of 90% glycerol and 10% substrate. The glycerol prevents the generated fluorescein from diffusing away from the microsphere reaction sites.

During the experiment, images in the encoded wavelengths are first taken. Since both DiIC and TRC are excited at 577 nm. Each microsphere's emissions at 670 nm, indicative of the presence of DiIC and 610 nm indicative of the presence of TRC were recorded using a 595 nm dichroic and an acquisition time of 5 seconds for the CCD 236.

Next, the distal end 212 of the fiber bundle is placed in a buffer and another image taken while illuminating the beams with 490 nm light. Emissions in the 530 nm fluorescein wavelengths were recorded with a 505 nm dichroic. In this case, a CCD acquisition time of one second was used. This process provides a background normalizing image. The buffer was removed and the fiber allowed to dry to avoid substrate solution dilution.

The substrate solution is then introduced and CCD images acquired every 30 seconds to a minute for 30 minutes. While illuminating the microspheres with 490 nm light and collecting emissions in the 530 nm range. Fiber is then placed back in the buffer solution and another background image captured. Those beads that generate a signal indicative of fluorescein production are decoded. Depending in the ratio of the intensity of light from the two reporter dyes, DiIC:TRC, the chemical functionality of the optically active beads may be decoded according to the following table.

| | |
|---|---|
| 0.617–1.08 | alkaline phosphatase bead |
| 3.188–5.725 | β-galactosidase bead |
| 0.183–0.243 | β-glucunonidese bead |

This process is then repeated for the remaining two substrates.

Figure 8A:
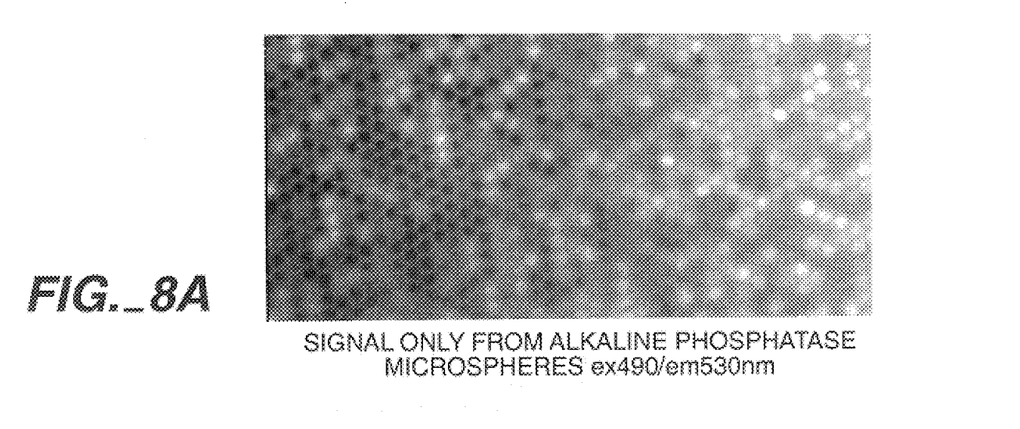
FIGS. 8A, 8B, and 8C are micrographs from alkaline phosphatase microspheres when exposed to fluorescein di-phosphate, at the fluorescein emission wavelength, at an encoding wavelength for DiIC, and at an encoding wavelength for TRC, respectively.
Figure 8B:
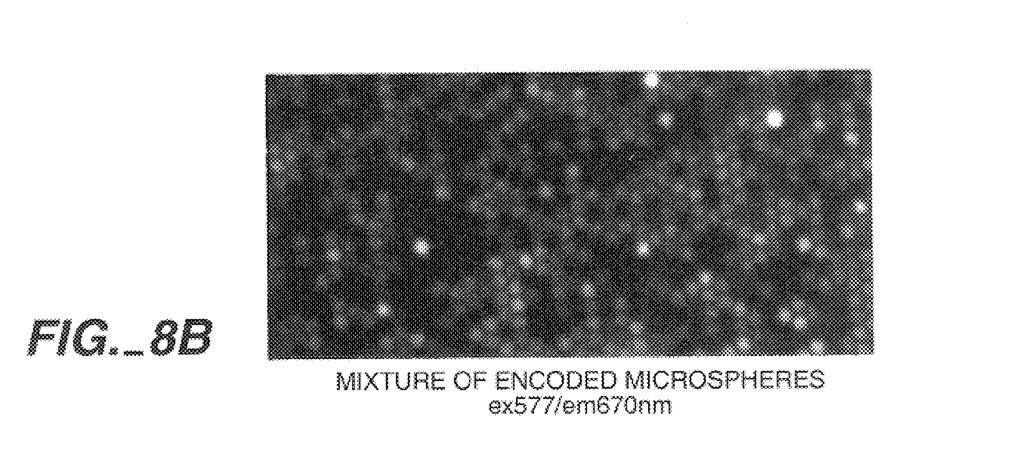
Figure 8C:
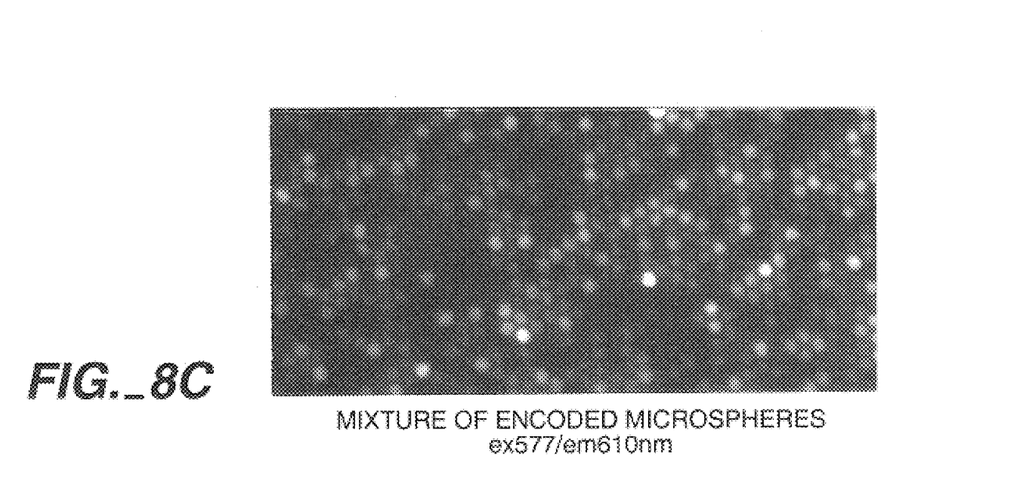

FIGS. 8A–8C are images generated by the CCD 236 when the bead populations are exposed to fluorescein di-phosphate. FIG. 8A illustrates the signals from the alkaline phosphatase microspheres when excited at 490 nm and recording emissions at 530 nm, emissions at this wavelength being indicative of fluorescein production. FIG. 8B shows the image captured by the CCD when the microspheres are excited at 577 nm and emissions at 670 nm are recorded. This wavelength is an encoding wavelength indicative of the concentration of DiIC on the microspheres. Finally, FIG. 8C shows the image when the microspheres are excited with 577 nm light and emissions in the 610 nm range are recorded being indicative of the concentration of TRC in the microspheres.

Figure 9A:
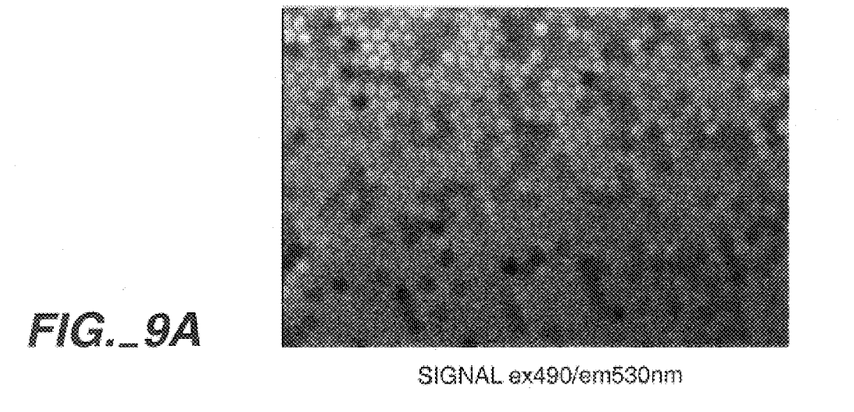
FIGS. 9A and 9B are micrographs showing the optical signal from β-galactosidase microspheres when exposed to fluorescein β-galactopyranoside at the fluorescein emission wavelength and at an encoding wavelength for DiIC, respectively.
Figure 9B:
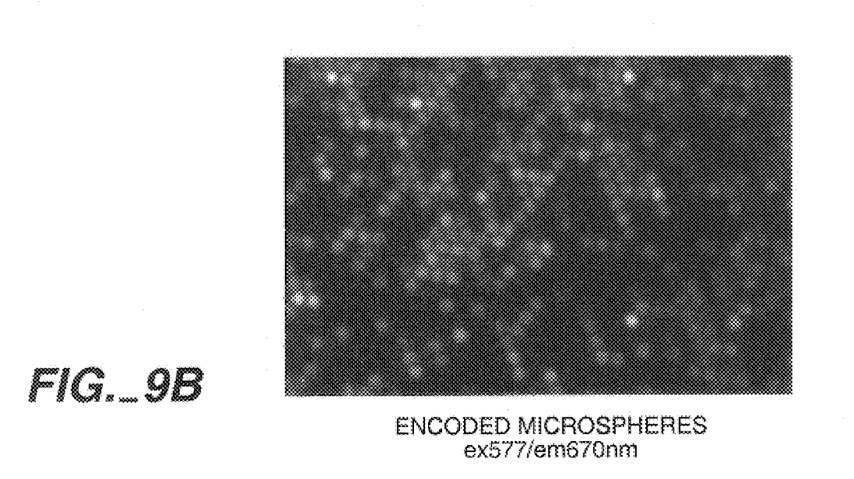

In a similar vein, FIGS. 9A and 9B are images when the microspheres are exposed to fluorescein d-β-galactosidase. FIG. 9A shows emissions at 530 nm indicative of the fluorescein production; and FIG. 9B shows light emitted at the 670 nm range indicative of the presence of DiIC.

These micrographs, FIG. 8A–8C and 9A–9B illustrate fluorescein production around the microspheres may be detected as an optical signature change indicative of reactions involving the chemical functionality of the microspheres. The micrographs also illustrate that the optical signatures may be decoded to determine the chemical functionalities on each microsphere.

Genosensor

Three separate subpopulations of beads were used. In subpopulation A, xrabbit antibodies (Ab) were affixed to the surface of the microspheres; in subpopulation B, xgoat antibodies were affixed to the microspheres; and in subpopulation C, xmouse antibodies were affixed to the microspheres. These three separate subpopulations were identified using a DiIC:TRC encoding ratio similar to that in the previously described experiment.

Figure 10A:
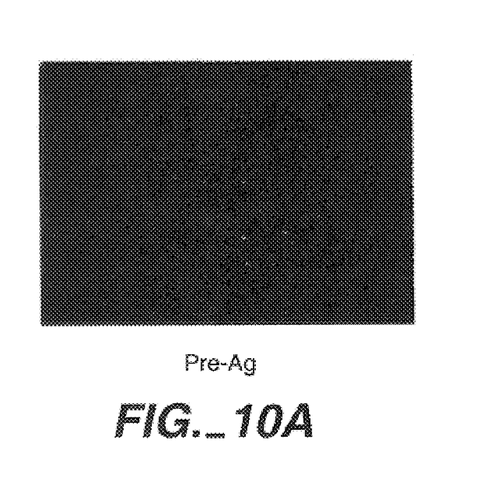
FIG. 10A and 10B are micrographs showing the optical response from xrabbit antibody microspheres prior to and post, respectively, exposure to fluorescein labeled antigens.
Figure 10B:
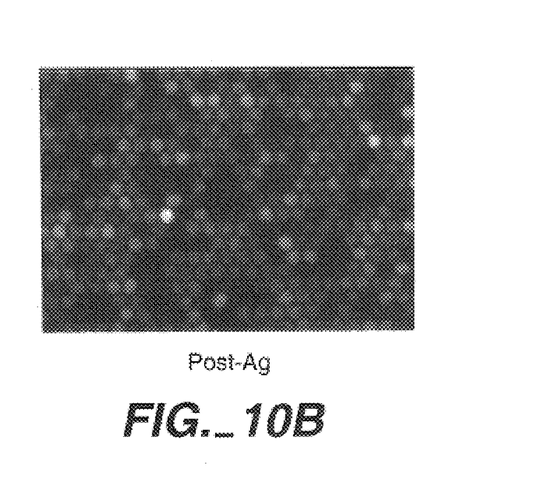

For the first step of the experiment, images at the encoded wavelengths were captured using 577 nm excitation and looking for emissions at 610 and 670 nm. After this decoding, the fiber was placed in a buffer and an image taken at 530 nm with 490 nm excitation. This provided a background normalizing signal at the fluorescein emission wavelength. Next, the fiber was placed in rabbit IgG antigen (Ag) which is fluorescein labeled. Images were then captured every few minutes at the 530 nm emission wavelength for fluorescein. FIGS. 10A and 10B are micrographs showing the image captured by the CCD prior to and subsequent to exposure to a rabbit antigen, which clearly show reaction of the selected micropheres within the population.

Note, if the fluorescein background from the antigen solution is too high to see the antibody-antigen signal, the fiber bundle may be placed in a buffer. This removes the background florescence leaving only the Ab–Ag signal.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A chemical analysis method, comprising
preparing separate subpopulations of beads, each subpopulation carrying chemical functionalities that change optical signatures of the beads in the presence of targeted analytes;
encoding optical signature of the beads in each subpopulation with a description of the chemical functionalities carried by that subpopulation;
combining the subpopulations to produce a system;
applying the system;
detecting changes in the optical signatures indicative of a presence of the targeted analytes; and
decoding optical signature of the beads to identify the chemical functionalities.

2. The method described in claim 1, wherein encoding the optical signatures with the chemical functionalities comprises doping the beads with fluorescent dyes.

3. The method described in claim 1, wherein encoding the optical signatures with chemical functionalities comprises attaching encoding dyes to the beads.

4. The method described in claim 1, wherein encoding the optical signatures with the chemical functionalities comprises controlling a ratio of at least two dyes carried by each bead.

5. The method described in claim 1, further comprising:
encoding the beads with the chemical functionalities by entrapping dyes within or attaching dyes to the beads; and
applying the chemical functionalities to the beads.

6. The method described in claim 1, further comprising enabling the chemical functionalities to produce an optically active species in the presence of targeted analytes to change the optical signature.

7. The method described in claim 1, further comprising changing the optical signature by the presence or absence of a fluorescent signal from the beads.

8. The method described in claim 1, further comprising enabling the chemical functionalities to hybridize.

9. An analytic chemistry sensor, comprising:
a bundle of optical fibers;
a population of beads carrying chemical functionalities at a distal end of the fiber optic bundle, light from individual bead being coupled into separate or groups of separate fibers of the bundle for transmission to the proximal end of the bundle.

10. The sensor described in claim 9, wherein each one of the beads is located within separate wells formed at terminal ends of optical fibers of the bundle.

11. The sensor described in claim 10, wherein the wells are formed by anisotropic etching of the cores of the optical fibers with respect to the cladding.

12. The sensor described in claim 9, further comprising a light source for exciting optically active chemicals bound to the chemical functionalities.

13. The sensor described in claim 9, wherein the population of beads includes separate subpopulations, each subpopulation carrying a different chemical functionality and an optically interrogatable code descriptive of the chemical functionality.

14. The sensor described in claim 13, further comprising a light source for exciting optically active chemicals bound to the chemical functionalities.

15. The sensor described in claim 13, wherein code of each subpopulation comprises fluorescent dyes.

16. The sensor described in claim 13, further comprising a filter and a frame capturing camera for detecting optical signatures indicative of a status of the chemical functionalities and optical signatures indicative of the encoding of the beads.

17. A method for constructing and using an analytic chemistry sensor, comprising:
forming wells at terminal ends of optical fibers within a bundle;
distributing beads carrying chemical functionalities within the wells; and
monitoring a status of the chemical functionalities from a proximal end of the bundle.

18. The method described in claim 17, wherein forming the wells comprises anisotropically etching of cores of the optical fibers with respect to cladding.

19. The method described in claim 17, further comprising forming a population of beads in the wells from separate subpopulations, each subpopulation carrying a different chemical functionality and an optically interrogatable code descriptive of the chemical functionality.

20. The method described in claim 19, further comprising randomly distributing the subpopulations within the wells.

21. The method described in claim 19, further comprising serially adding the subpopulations to the wells.

22. A composition comprising a plurality of optical fibers in an optical fiber array and a population of microspheres, wherein said optical fibers have wells at a first terminal end of said fibers and a plurality of said wells contain at least one microsphere.

23. A composition comprising:
   a) a substrate;
   b) a population of microspheres comprising separate subpopulations, each subpopulation comprising:
      i) a chemical functionality for testing for interaction with a target analyte; and
      ii) an encoding optical signature that can be used to identify said chemical functionality;
   wherein said microspheres are distributed on said substrate.

24. A composition according to claim 23 wherein said substrate is an optical fiber array comprising a plurality of individual fibers and said microspheres are located within wells at a first terminal end of said fibers.

25. A composition according to claim 23 wherein said encoding optical signature comprises at least one chromophore.

26. A composition according to claim 23 wherein said encoding optical signature comprises at least one fluorescent dye.

27. A composition according to claim 26 wherein said fluorescent dye is entrapped within said microspheres.

28. A composition according to claim 26 wherein said fluorescent dye is attached to said microspheres.

29. A composition according to claim 26 wherein said encoding optical signature comprises a ratio of at least two or more fluorescent dyes.

30. A composition according to claim 26 wherein at least a first subpopulation of microspheres is a different size than a second subpopulation of microspheres.

31. A composition according to claim 24 wherein the individual fibers of said array are of uniform size.

32. A composition according to claim 24 wherein the individual fibers of said array are of a plurality of sizes.

33. A composition according to claim 23 wherein said chemical functionality is a nucleic acid.

34. A composition according to claim 23 wherein said chemical functionality is an antibody.

35. A composition according to claim 23 wherein said chemical functionality is an enzyme.

36. A composition according to claim 23 wherein said chemical functionality is selected from the group consisting of fluorophores, chromophores, phosphors, pH indicators, cation indicators, anion indicators, metal ion indicators, ion salt indicators, oxygen indicators and carbon dioxide indicators.

37. A composition according to claim 23 further comprising at least one target analyte interacting with at least one chemical functionality.

38. A composition according to claim 37 wherein said target analyte comprises at least one fluorophore.

39. A method of determining the presence of a target analyte in a sample comprising:
   a) contacting said sample with a composition comprising:
      i) a substrate;
      ii) a population of microspheres comprising separate subpopulations, each subpopulation comprising:
         1) a chemical functionality for testing for interaction with a target analyte; and
         2) an encoding optical signature that can be used to identify said chemical functionality;
      wherein said microspheres are distributed on said substrate; and
   b) determining the presence or absence of the target analyte.

40. A method according to claim 39 wherein said substrate is an optical fiber array comprising a plurality of individual fibers and said microspheres are located within wells at a first terminal end of said fibers.

41. A method according to claim 39 further comprising identifying the location of each subpopulation on said substrate.

42. A method according to claim 39 wherein said encoding optical signature comprises at least one chromophore.

43. A method according to claim 39 wherein said encoding optical signature comprises at least one fluorescent dye.

44. A method according to 43 wherein said fluorescent dye is entrapped within said microspheres.

45. A method according to claim 39 wherein said encoding optical signature comprises a ratio of at least two or more fluorescent dyes.

46. A method according to claim 39 wherein at least a first subpopulation of microspheres is a different size than a second subpopulation of microspheres.

47. A method according to claim 40 wherein the individual fibers of said array are of uniform size.

48. A method according to claim 40 wherein the individual fibers of said array are a plurality of sizes.

49. A method according to claim 39 wherein said target analyte is a nucleic acid.

50. A method according to claim 39 wherein said chemical functionality is a nucleic acid.

51. A method according to claim 39 wherein said chemical functionality is an enzyme.

52. A method according to claim 39 wherein said chemical functionality is an antibody.

53. A method according to claim 39 wherein said chemical functionality is selected from the group consisting of fluorophores, chromophores, phosphors, pH indicators, cation indicators, anion indicators, metal ion indicators, ion salt indicators, oxygen indicators and carbon dioxide indicators.

54. A method of making a composition comprising:
   a) forming wells at a terminal end of an optical fiber array; and
   b) distributing microspheres within said wells, wherein said microspheres comprise separate subpopulations, each subpopulation comprising:
      i) a chemical functionality for testing for interaction with a target analyte; and
      ii) an encoding optical signature that can be used to identify said chemical functionality.

55. A method according to claim 54 wherein said forming comprises anisotropically etching the cores of the individual fibers of said array.

56. A method according to claim 55 wherein said distributing comprises serially adding said subpopulations to said wells.

57. A sensor comprising:
   a) an array of optical fibers;
   b) a population of microspheres comprising separate subpopulations, each subpopulation comprising:
      i) a chemical functionality for testing for interaction with a target analyte; and
      ii) an encoding optical signature that can be used to identify said chemical functionality;
   wherein said microspheres are distributed on a first terminal end of said array; and
   c) a light source.

58. A sensor according to claim 57 further comprising a light detector.

* * * * *

UNITED STATES PATENT AND TRADEMARK OFFICE
CERTIFICATE OF CORRECTION

PATENT NO.    : 6,023,540            Page 1 of 1
DATED         : February 8, 2000
INVENTOR(S)   : David R. Walt and Karri Lynn Michael It is certified that error appears in the above-identified patent and that said Letters Patent is hereby corrected as shown below:

Column 1,
After the title "FIBER OPTIC SENSOR WITH ENCODED MICROSPHERES", insert the following paragraph:

-- This invention was made with government support under N00014-95-1-1340 awarded by the Department of the Navy, Office of Naval Research. The government has certain rights in the invention. --

Signed and Sealed this

Twenty-first Day of May, 2002

Attest:

Attesting Officer

JAMES E. ROGAN
*Director of the United States Patent and Trademark Office*